(12) United States Patent
Spillert

(10) Patent No.: US 6,245,573 B1
(45) Date of Patent: Jun. 12, 2001

(54) RAPID ASSESSMENT OF THE COAGULANT ACTIVITY OF BLOOD

(75) Inventor: Charles R. Spillert, West Orange, NJ (US)

(73) Assignee: University of Medicine and Dentistry of New Jersey, Piscataway, NJ (US)

( * ) Notice: Subject to any disclaimer, the term of this patent is extended or adjusted under 35 U.S.C. 154(b) by 0 days.

(21) Appl. No.: 09/022,449

(22) Filed: Feb. 12, 1998

(51) Int. Cl.$^7$ .................................................. G01N 33/86
(52) U.S. Cl. ........................... 436/69; 436/73; 436/74; 436/80; 436/81; 422/61; 422/73; 73/64.41
(58) Field of Search ................................. 436/18, 63, 69, 436/73, 74, 80, 81; 422/61, 68.1, 73; 435/2, 13; 73/54.01, 64.41

(56) References Cited

U.S. PATENT DOCUMENTS

| | | | | |
|---|---|---|---|---|
| 4,434,234 | * | 2/1984 | Adams et al. | 436/86 |
| 4,705,756 | | 11/1987 | Spillert et al. | 436/64 |
| 4,814,247 | | 3/1989 | Spillert et al. | 436/69 |
| 4,900,679 | | 2/1990 | Spillert et al. | 436/69 |
| 5,051,357 | | 9/1991 | Hassouna | 435/13 |
| 5,055,412 | * | 10/1991 | Proksch | 436/69 |
| 5,314,695 | | 5/1994 | Brown | 424/450 |
| 5,348,891 | * | 9/1994 | Van Es et al. | 436/525 |
| 5,403,716 | | 4/1995 | Matsuzawa et al. | 435/7.9 |
| 5,413,786 | * | 5/1995 | Anraku | 514/185 |
| 5,472,850 | | 12/1995 | Morrissey | 435/13 |
| 5,525,478 | | 6/1996 | Matschiner | 435/13 |
| 5,569,590 | | 10/1996 | Speck | 435/13 |
| 5,625,036 | | 4/1997 | Hawkins et al. | 530/381 |
| 5,700,634 | * | 12/1997 | Speck | 435/4 |
| 5,705,396 | | 1/1998 | Fickenscher et al. | 436/69 |

FOREIGN PATENT DOCUMENTS 0697463    8/1995   (EP).

OTHER PUBLICATIONS

Goodwin et al. *Biochemical Journal*, vol. 308, pp. 15–21, 1995.*
Kaneko et al, 1994, Br J Haem, 87:87–93.
Spillert and Lazaro, 1993, J Nat Med Assoc, 85:611–6.
Falanga et al., Int. J. Cancer, 39:774–77 (1987).
Gordon et al., Blood, 6:1261–65 (1985).
Falanga et al., Leukemia, 8(1):156–59 (1994).

* cited by examiner

*Primary Examiner*—Maureen M. Wallenhorst
(74) *Attorney, Agent, or Firm*—Klauber & Jackson

(57) ABSTRACT

This invention relates to diagnostic methods and test kits for rapidly assessing the coagulant activity of blood by measuring the rate of blood clotting in the presence of certain metal ions. A modulator of coagulation may also be included. The coagulation activity of the blood of the patient in the presence of metal ions and an optional modulator is an indication of the presence or development of certain pathological conditions relating to the procoagulant activity of blood, including platelet function. The effect of metal ions on the viscosity of blood is also diagnostically useful.

14 Claims, No Drawings

RAPID ASSESSMENT OF THE COAGULANT ACTIVITY OF BLOOD

FIELD OF THE INVENTION

This invention relates to diagnostic methods and test kits for rapidly assessing the coagulant activity of blood by measuring the rate of blood clotting in the presence of certain metal ions. The coagulation activity of the blood of the patient is an indication of the presence or development of certain pathological conditions.

BACKGROUND OF THE INVENTION

The propensity for blood to clot too rapidly is an important prognosticator for the development of, progression of, and recovery from a number of serious pathological conditions whose pathogeneses either arise directly from or are modulated by the blood clotting process. These diseases include heart attack, stroke, coronary artery disease, deep vein thrombosis, and pulmonary embolism, among others. Of these diseases, coronary artery disease is the leading cause of mortality in the United States. Furthermore, certain clinical conditions may predispose patients to undergo adverse clotting phenomena, such as vascular disease, surgery, trauma, malignancy, prosthetic vascular devices, general anesthesia, pregnancy, use of oral contraceptives, systemic lupus erythematosus, and infection. Often, patients with acute conditions suspected of resulting from clotting abnormalities appear in the emergency room. Means for rapidly detecting in a blood sample the propensity for clot formation may help rule in or rule out thrombotic events and coagulopathies and improve the delivery of emergency health care to those in need, while also offering early identification of patients who may progress to potentially lethal clotting pathology. It has been estimated that 80% of all deaths are associated with a disease in which abnormal clotting phenomena occur, principally of blood that clots too quickly.

Blood clotting is a complex process involving multiple initiators, cascades of activators, enzymes, and modulators which ultimately lead to the formation of fibrin, which polymerizes into an insoluble clot. Classically, the propensity for blood to clot is measured manually or automatedly by measuring the time taken for a sample of plasma or blood to form insoluble fibrin strands or a clot. Clot formation may be detected visually, by observing the formation of fibrin strands, or by automated means such as by changes in viscosity or by photo-optical detection of the clot in plasma-based assays. The measurement of clotting time may be made immediately on freshly drawn blood without the need for addition of anticoagulants, or may be made on blood containing a calcium-binding anticoagulant such as citrate by adding a calcium salt to reverse the anticoagulant effect; this latter determination is referred to as recalcification time. Determination of the coagulation time has been most commonly used for the diagnosis of diseases such as hemophilia, von Willebrand's disease, Christmas disease and hepatic diseases, wherein abnormally prolonged clotting times are usually diagnostic. Typical methods for the measurement of blood coagulation time which have been conventionally employed include those relying on the measurement of prothrombin time (PT), the measurement of activated partial thromboplastin time (APTT), the measurement of thrombin time, as well as the fibrinogen level test. Detection of a thrombotic event also may be performed by measuring the level of soluble fibrin or fibrin degradation products in circulation. Although many impending serious conditions involving abnormal blood coagulability might be detectable prior to the occurrence of acute, lethal or near-lethal events, altered blood coagulability measurement methods are not presently sensitive enough to be diagnostically valuable in identifying all but the most abnormal coagulation samples.

The PT and APTT tests are not sensitive enough to be used to detect hypercoagulable states, and are generally used to detect conditions with prolonged clotting times. These tests are usually performed on plasma, which does not contain activated platelets and monocytes, both of which may contribute significantly to altered coagulation states. Furthermore, these tests utilize reagents added to the sample which are procoagulants themselves and reduce the clotting time of plasma from about six minutes to values of about 12 seconds, and 38 seconds, for PT and APTT, respectively. By excluding the influence of the cellular components of whole blood, such as monocytes, these popular measurement methods for clotting time using plasma as described above do not fully provide maximum predictive and diagnostic value for thrombotic events that may be modulated by the cellular components of blood. Furthermore, the monitoring of anticoagulant therapies such as heparin and warfarin would be improved if the coagulability of whole blood, rather than plasma alone, were measured. The presence of therapeutically-administered anticoagulants modulates coagulability through cellular as well as soluble (plasma) blood constituents.

One important initiator and modulator of the blood clotting process is a procoagulant enzyme called tissue factor present which may be present in and on the surfaces of both endothelial cells, which line the vasculature, and monocytes, which circulate in blood. Increased expression of tissue factor by these cell types has been linked to many thrombotic disorders and pathologic states. The ability of monocytes to generate tissue factor is well known. However, the majority of monocyte membrane-associated tissue factor is not in an enzymatically active form that can initiate clotting; in order to become active, tissue factor must form an active complex with another of the clotting factors, Factor VII or its activated form, Factor VIIa. The Tissue Factor:Factor VIIa complex may then activate zymogens Factor IX and Factor X to their enzymatically active forms, Factors IXa and Xa. Factor Xa combines with prothrombin to yield the prothrombinase complex (active procoagulant), yielding thrombin which cleaves fibrinogen, finally yielding fibrin which forms the clot. The level on blood monocytes of the inactive, latent form of tissue factor, and its proclivity to become activated and eventually to form the prothrombinase complex, is a diagnostically useful parameter for identifying patients at risk of undergoing thrombotic events. Tissue factor has been found on circulating monocytes from patients with cancer, infections, and thrombotic disorders such as heart attack and stroke.

Methods for the direct measurement of tissue factor level have been described. In addition to immunoassay procedures, such as that described in U.S. Pat. No. 5,403,716, the exposure of whole blood to endotoxin, as described in U.S. Pat. No. 4,814,247 and as described by Spillert and Lazaro, 1993, J. Nat. Med. Assoc. 85:611–616, provides within several hours an assessment of tissue factor levels. In this invention, the modified recalcification time is measured in a blood sample exposed to endotoxin for a period of time adequate for active tissue factor to be generated by monocytes in the sample.

Kaneko et al. (1994, Br. J. Haem. 87:87–93) determined that a monocyte leukemia cell line (U937 cells) when incubated with mercuric ion or silver ion in tissue culture had increased generation of tissue factor-dependent procoagulant activitv. This increased procoagulant activity was postulated to be a result of changes of cell surface phosphatidylserine and other membrane changes.

The invention described herein offers a rapid method for assessment of the thrombotic activity of blood by measuring blood clotting time after exposure to certain heavy metal ions such as those of mercury and silver.

SUMMARY OF THE INVENTION

It is a principal object of the present invention to provide a method to rapidly assess the overall coagulant properties of a sample of a patient's blood by exposing an aliquot of the blood sample to at least one metal ion, and subsequently measuring clotting time of the aliquot by standard methods. When measured on whole blood, the resultant clotting time represents the overall coagulant activity of the combination of the plasma and cellular components of the blood, and is indicative of existing or impending pathology arising from abnormal coagulability of the blood. The measurement preferably includes the clotting time of a control sample of whole blood without the addition of metal ion, to which the clotting time of the aliquot containing the metal ion is compared. Optionally, one or more additional aliquots are prepared to which are added one or more other metal ions. The preferred metal ions are mercuric and silver ion, although others such as lead, cadmium, copper and tin also provide diagnostically-useful information. Metal ions are provided as reagents comprising solutions of their salts, preferably aqueous solutions.

In the practice of the present invention, a whole blood sample is collected from a patient and immediately thereafter divided into aliquots. To one aliquot is added mercuric ion, and to another optional aliquot, silver ion. Preferably, a sample of vehicle is added to another aliquot which is used as a control. Following addition of the metal ion reagent or reagents, the clotting time of the blood samples are measured by standard methods. This method using freshly drawn blood provides the fastest measurement, as native blood is used which initiates clotting after being removed from the patient. In an alternate and preferred method, blood is collected from the patient and mixed immediately with an anticoagulant, such as citrate, oxalate, or EDTA, which prevents the blood from clotting by complexing with calcium ions which are necessary for coagulation. The blood can be analyzed immediately thereafter, or stored for a period of time before the analysis is performed. The anticoagulated blood is divided into aliquots. To one aliquot is added mercuric ion reagent, and to another optional aliquot, silver ion reagent. Preferably, a sample of vehicle is added to another aliquot which is used as a control. Following an optional incubation period, calcium salt is added to the aliquots, and the clotting time determined by standard methods. Addition of calcium salt initiates the blood clotting process in the anticoagulated blood.

The utility of the present invention may be achieved by the use of either native blood or anticoagulated blood. In some instances, plasma may be utilized. Factors such as the urgency of need for a diagnosis and the availability of instrumentation may govern what type of sample is used. The selection does not detract from the utilities of the invention described herein. The choice of method used for determining clotting time is not critical to the practice of the invention.

It is another object of the present invention to provide for a method for measuring the effectiveness of anticoagulant therapy, such as that of warfarin or low molecular weight heparin, by measuring the coagulant activity in a sample of whole blood by first exposing a sample of whole blood to metal ions, followed by measuring the clotting time of the blood sample by standard methods. The value of the clotting time or the differences between the control value and those of the metal ions, is useful in monitoring anticoagulation therapy. Mercuric and silver ions are preferred, although other metal ions such as lead, cadmium, copper and tin also provide diagnostically-useful information.

It is a further objective of the present invention to provide for a method to monitor the recovery of a patient from a condition related to adverse blood coagulation by monitoring the clotting of blood in accordance with the methods described herein.

It is yet another objective of the present invention to provide diagnostic kits for the measurement of the clotting time of whole blood and plasma in the presence of metal ion. Metal ions are provided as reagents comprising solutions of their salts, preferably aqueous solutions. Mercuric ion and silver ion reagent are preferred components of the kit.

It is yet a further object of the present invention to provide method and kits for determining viscosity of plasma or whole blood after exposure to metal ion.

These and other aspects of the present invention will be better appreciated by reference to the following drawings and Detailed Description.

DETAILED DESCRIPTION OF THE INVENTION

Factors which alter the coagulability of blood cause a range of pathologies. In particular, factors which increase the coagulability or prothrombotic potential of blood are in most instances highly undesirable and may lead to serious pathologic states, for example, heart attack, stroke, coronary artery disease, deep vein thrombosis, and pulmonary embolism. Furthermore, certain clinical conditions may predispose patients to undergo adverse clotting phenomena, such as vascular disease, surgery, trauma, malignancy, the presence of prosthetic vascular devices, general anesthesia, pregnancy. use of oral contraceptives, systemic lupus erythematosus, and infection. These conditions alter the coagulation state of the blood to cause the prothrombotic pathways to predominate and intensify, as compared with the protective anticoagulant pathways. On the other hand, the objective of anticoagulant therapy is to decrease the coagulability or prothrombotic potential of blood, in order to avert the adverse consequences of a pathological state which promotes blood coagulability.

The overall coagulability of blood is governed by factors contributed by both the soluble (plasma) portion of blood as well as that provided by the cellular portion of blood. Traditional measures of clotting or blood coagulability typically use plasma, in the measure of prothrombin time (PT) and active partial thromboplastin time (APTT), among other measures of blood coagulability. However, these measures using plasma omit contributions to blood coagulability provided by the cellular components of blood (platelets and white blood cells), and hence, provide limited diagnostically-useful information. Furthermore, the propensity for certain cellular components of blood to modulate the blood clotting process may not be apparent when clotting time is measured on a whole blood sample. One example is the contribution of tissue factor in the measurement of blood coagulability. As described above, tissue factor is an initiator and modulator of blood coagulation, and may be present on vascular endothelial cells and circulating blood monocytes; elevated levels are associated with pathologic states. It is present on monocytes predominantly in an inactive or latent form, and must become activated before it may participate in the initiation of the clotting process. Latent tissue factor present on the cell membrane of monocytes may become activated and promote blood coagulation in vivo, and hence this activity may be responsible for pathological conditions; yet coagulation tests on whole blood may not be sensitive to this important component of the overall coagulability of blood. In addition to tissue factor, other components present in or on the cellular components of blood may also modulate blood coagulability and also contribute to the propensity for blood to clot in vivo. It is desirable to provide an in vitro assessment of the overall coagulability of blood which represents the propensity for blood to clot in vivo, to provide the health care professional with diagnostically and clinically useful data for assessing the patient's condition, selecting the proper course of therapy, as well as monitoring the rate and effectiveness of surgical and non-surgical therapies. A rapid assessment method of overall blood coagulability which sensitively addresses the contributions of both the cellular and noncellular components of blood is heretofore unavailable.

The invention described herein provides a method for measuring the overall coagulability of whole blood. This is achieved by exposing the blood sample to metal ions, preferably mercuric ions, and separately silver ions, before or during the measurement of clotting time.

It has been found that the coagulability of whole blood the presence of mercury salts is indicative of coagulation factors contributed by cellular components of the blood; likewise, the coagulability of whole blood in the presence of silver salts is indicative of coagulation factors contributed by both the plasma and cellular components of blood. By measuring blood coagulability in the presence of mercuric ions, and separately in the presence of silver ions, as compared to a control without metal ions, an assessment of the overall coagulability of whole blood may be obtained from which diagnostic and clinical utility may be drawn. individually, the coagulability with each of the metal ions provides certain diagnostically and clinically useful information. Other metal ions such as lead, cadmium, copper and tin may also provide diagnostically-useful information.

While the theory of the invention is not fully understood, nor do Applicants wish to be bound by any theory of the invention, it is believed that the addition of the metal ions of the present invention to whole blood prior to and/or during the coagulation process alters the coagulability of blood which more closely reflects the thrombotic potential of blood while in circulation. One important cellular factor responsible for modulating coagulability of blood is the monocyte-generated protein, tissue factor. As described above, tissue factor is a procoagulant (prothrombotic) enzyme, present on the surface of these cell types. It is normally present in an inactive state, but becomes activated under certain conditions in vivo, promoting the coagulability of blood and thus may contribute to pathology. Traditional measures of blood coagulability using plasma do not measure the potential for monocyte tissue factor to become activated and increase the coagulability of blood. Theoretically, the exposure of monocytes to mercury salts activates the latent tissue factor that in vivo would contribute to prothrombotic activity; thus the measure of clotting time in the presence of mercuric ions represents any increased procoagulant activity resulting from latent tissue factor. As will be seen in the examples below, the increased coagulability of whole blood in the presence of mercuric ions correlates with pathological states deriving from aberrant blood coagulability.

The same methods as described above for measuring the clotting time in the presence of mercuric ions also applies to silver ions. While the Applicants do not wish to be bound by theory, the theoretical basis for the effect of silver salts in altering blood clotting involves a different mechanism than that of mercuric ions, and the diagnostic and clinical utility of the value obtained from silver ions is different. Silver salts appear to interfere with the activity of anticoagulant proteins present in the blood sample, possibly by interacting with sulfhydral groups present on anticoagulant proteins or their binding partners, for example, antithrombin, protein C, and protein S. Silver ion may react with sulfur-containing functional groups or with amino, carboxyl, phosphate groups, among others. By interfering with anticoagulant proteins, the addition of silver salts to a whole blood sample decreases the clotting time, and this decrease appears to be related to the level of anticoagulants relative to procoagulants present in the blood sample. Silver ion, unlike mercuric ion, shortens the clotting times of both whole blood and plasma. Silver ion is relatively non-toxic, as is employed in topical antibacterial creams such as that containing silver sulfadiazine for burn patients, and is also taken orally as a smoking deterrent. Its propensity as a procoagulant has been known as it has been used historically as a cauterizing agent, to stop external bleeding, such as nosebleed.

Furthermore, in contrast to the above-cited modified recalcification time test in which endotoxin incubated with a whole blood sample induces the synthesis of tissue factor which then influences the coagulant properties of the blood sample, the method of the present invention does not measure the effect on blood coagulability resulting from tissue factor synthesis, but the influence on blood coagulability by tissue factor present in a latent form, as it has been found that in the presence of mercuric ions, no protein synthesis by monocytes is required to demonstrate altered clotting time. Theoretically, mercuric ion transforms latent tissue factor into an active form, and the assay measures only latent plus active tissue factor, and not that which may be synthesized de novo during the incubation period.

The method of the present invention may be performed with fresh whole blood, to which metal ions are added, preferably mercuric and optionally also silver, followed by measurement of the coagulability of the blood sample by standard methods. Alternatively, a blood sample may be collected in the presence of an anticoagulant, such as citrate, oxalate, EDTA, etc. Subsequently, metal ions such as mercuric ions or silver ions may be added, followed by an optional incubation period, and then the coagulability of the blood determined by standard methods. In the instance where then blood is collected with an anticoagulant, the effect of the anticoagulant in the blood sample must be reversed at the time that blood coagulability or clotting time is measured. This is accomplished by the addition of a calcium salt, such as calcium chloride. The measurement of clotting time on a sample of anticoagulated blood by the addition of a calcium salt to reactivate the clotting process is referred to as the recalcification time.

The metal ions of the present invention include, but are not limited to, mercuric ion, silver ion, ion, cadmium ion, copper ion, barium ion, tin ion, selenate ion and tungstate ion. Mercuric and silver ions are preferred. These metal ions are provided in the form of a reagent, preferably a soluble metal salt in aqueous solution, such as mercuric chloride or silver nitrate. The concentration of the metal ion salt in the reagent is provided so that it may be easily added to the blood sample to provide the proper final concentration in order to carry out the method of the present invention.

Determination of clotting time by the method of the present invention may also be performed in the presence of certain additional compounds which may also provide useful information of diagnostic and clinical utility in the identification and monitoring of certain disease states related to thrombosis. Compounds such as homocysteine, tissue factor, Russells' viper venom and other procoagulant venoms is contemplated. Other compounds which modulate the clotting process are also contemplated. Homocysteine is a metabolite that is present in circulation at increased levels in patients with a predisposition to atherosclerosis. An elevated homocysteine level is a marker for increased thrombotic complications. However, when homocysteine is added to blood and the clotting time determined, it was found to have no intrinsic procoagulant effect. When homocysteine was added to bloods containing either silver or mercuric ions, the reduction in clotting time was greater than that induced by metals alone. Thus, the use of these metals enabled the detection of a thrombotic state induced by homocysteine which was not otherwise detectable.

Other modulators of the clotting process contemplated for use in the present invention include procoagulants such as tissue factor, prothrombotic venoms, thrombin, platelet activating factor, fibrinogen, kaolin, celite, adenosine diphosphate, arachidonic acid, collagen, and ristocetin. Factors with anticoagulant activity useful as modulators of the clotting process of the present invention include Protein C, protein S, antithrombin III, thrombomodulin, tissue plasminogen activator, urokinase, streptokinase, and Von Willebrand Factor. Addition of therapeutic drugs which may modulate the coagulant activity of blood may also be used as modulators in the present invention. In addition, cancer cell extracts and amniotic fluid may also be used as modulators.

Tissue factor, as described above, is an initiator of the blood clotting process. Addition of tissue factor to whole blood in accordance with the methods of the present invention provides information related to the presence and or activity of other critical factors in the clotting process. Russells' viper venom is a procoagulant that accelerates clotting by activating Factors V and X. The synergistic procoagulant effects of Russells' viper venom (which activates Factor X directly) and ecarin (activates prothrombin directly) with mercuric and/or silver ion enable, in part, the determination of coagulation pathway disorders in humans with different diseases. They may also be of aid in monitoring anticoagulant therapies, such as those using low molecular weight heparin, hirudin, oral anticoagulants, or thrombolytic agents such as tissue plasminogen activator and streptokinase.

The method for measuring whole blood clotting time in the present invention may be any of a number of procedures available in the art, including manual, semiautomated and automated procedures, and their corresponding equipment or instruments. For example, the SONOCLOT® Coagulation Analyzer, available from Sienco, Inc. measures viscoelastic properties as a function of mechanical impedance of the sample being tested. Such analysis is very sensitive to fibrin formation, thereby providing improved sensitivity and reproducibility of results. Another device, the thrombelastograph (TEG), which can also be used for measuring viscoelastic properties. An example of this type of instrumentation is the computerized thrombelastograph (CTEG), from Haemoscope Corp. The SONOCLOT(R) and CTEG are capable of recording changes in the coagulation process by measuring changes in blood viscosity or elasticity, respectively. A complete graph of the entire process is obtained. Other instruments such as the HEMOCHRON(R) measure clotting time but do not provide a graph of the change in a clotting parameter as a function of time.

In one embodiment of the invention, where the assays are performed on an emergent basis, for example, in the emergency room on a patient suspected of having an acute thrombotic event such as a heart attack or stroke, no anticoagulant need be used and the assays may be performed directly with a fresh blood sample. The necessary reagents may be preloaded into the coagulation analyzer, and the clotting times in the presence of mercuric ions and, separately, silver ions determined, preferably along with that of a control sample without the addition of metal ions. Better reproducibility is obtained if the blood is first collected with an anticoagulant that binds calcium, such as citrate, oxalate, EDTA, etc., and the clotting times made subsequently under traditional laboratory conditions. In order to initiate clotting in a sample containing one or more of these anticoagulants, calcium salt must be added. Addition of calcium salts to overcome the anticoagulant activity initiates the clotting process, and the time for the formation of fibrin polymers referred to in this instance as the recalcification time. As an example of the performance of the assays on anticoagulated blood, 5 $\mu$l of 5% mercuric chloride is added to a 495 $\mu$l sample of citrated blood; 5 $\mu$l of 5% silver nitrate is added to a second 495 $\mu$l sample of citrated whole blood, and 5 $\mu$l of water is added to a third sample. After mixing the samples, they are placed in a 37 C incubator for 10 minutes. After the optional incubation period, 300 $\mu$l of each sample is mixed with 40 $\mu$l of 0.1 M calcium chloride, and the recalcification time (the time necessary for fibrin to form) is measured by automated instrumentation. The difference between the recalcification time of the control versus the samples containing metal ions is used diagnostically to indicate if the patient has abnormal blood coagulability and is in need of medical intervention.

In a further embodiment of the invention, a test kit is provided for determining coagulability in which metal ion and other reagents at the proper concentrations are provided in order to determine the clotting or recalcification time using clotting time instrumentation.

Another utility of the present invention is in identifying abnormalities in the viscoelastic properties of whole blood or plasma. The changes in the relative viscosity of whole blood or plasma induced by the addition of metal ions is diagnostically useful. Metal ion reagent may be added to a sample of anticoagulated plasma or whole blood, and after an optional incubation period, the viscosity determined, preferably along with a control that does not contain a metal salt.

The following examples are presented in order to more fully illustrate the preferred embodiments of the invention. They should in no way be construed, however, as limiting the broad scope of the invention.

General methodology. Fresh blood or anticoagulated blood collected with citrate was used. Clotting time was determined using a SONOCLOT(R) Coagulation Analyzer. Incubation times of blood specimens with the metal ion reagents of the present invention is carried out for ten minutes, unless indicated otherwise, to insure the sample is at or near 37° C., the required temperature for all clotting tests. In some examples, no preincubation of the metal ion with the blood or plasma sample was performed. After incubation, calcium salt is added to the citrated whole blood sample to initiate clotting, and the clotting time determined. Bloods are not exposed to any procoagulant surfaces ex vivo. The clotting time of anticoagulated blood wherein clotting is initiated by addition of calcium salt is often specifically referred to as recalcification time, and generally referred to as clotting time.

Mercuric ion reagent is in the form of 5% $HgCl_2$ (184 mM) and silver ion reagent 5% $AgNO_3$ (294 mM) in aqueous solution. A ratio of 5 μl metal ion solution plus 495 μl citrated whole blood, or 10 μl metal ion solution plus 990 μl citrated whole blood, is used, unless otherwise indicated. As a control, water was used in place of the metal ion solution. To initiate clotting by recalcification, 300 μl of the citrated whole blood/metal ion solution is mixed with 40 μl 0.1 M $CaCl_2$.

EXAMPLE I

COMPARISON OF RECALCIFICATION TIME OF CITRATED PLASMA TO THAT OF CITRATED WHOLE BLOOD, IN THE ABSENCE AND PRESENCE OF MERCURIC ION

The recalcification time of citrated plasma and citrated whole blood samples from the same patients were evaluated in the absence of mercuric ion (n=12 samples). The plasma recalcification time was 634±260 seconds (mean±standard deviation), whereas that of whole blood was 426±131 seconds. The reduced recalcification time of whole blood versus plasma is attributed to procoagulants associated with the cellular portion of blood, principally platelets and monocytes.

The effect of mercuric ion on the recalcification time of plasma and whole blood was evaluated on a different set of patient samples, following the General Methodology above. The results are presented as follows.

| Sample treatment | Recalcification time (seconds) | |
|---|---|---|
| | Citrated whole blood | Plasma |
| Control | 281 ± 51 | 424 ± 120 |
| Mercuric Ion | 187 ± 19 | 1701 ± 649 |

In citrated whole blood, mercuric ion significantly reduces the recalcification time when compared to control. However, in plasma, mercuric ion significantly prolongs recalcification time. Thus, the effect of mercuric ion during the clotting of whole blood is to increase any procoagulant effect contributed by the cellular components of the blood.

These experiments demonstrate that the cellular components of blood contribute to the procoagulant activity of blood and that the addition of mercuric ion further increases the procoagulant activity thereby reducing the clotting time.

EXAMPLE II

EFFECT OF INCUBATION TIME ON MERCURIC ION-ACTIVATED RECALCIFICATION TIME

Following the General Methodology above, whole blood was mixed with mercuric ion and incubated for 10, 20, and 30 minutes before addition of calcium chloride and measurement of recalcification time. Ten samples were evaluated per time point. The following recalcification times were measured:

| Incubation time with $HgCl_2$ (minutes) | Recalcification Time (minutes) |
|---|---|
| Control (no $HgCl_2$), 10 minutes | 4.6 ± 1.1 |
| 10 | 2.8 ± 0.8 |
| 20 | 3.1 ± 0.8 |
| 30 | 3.1 ± 1.0 |

Thus, increasing incubation time does not change the mercury-ion activated recalcification time. The desired effect is achieved after 10 minutes of incubation, when compared to the control.

EXAMPLE III

EFFECT OF MERCURIC ION CONCENTRATION ON RECALCIFICATION TIME OF CITRATED WHOLE BLOOD

Following the General Methodology above, three final concentrations of mercuric chloride were tested: 1800 μM, 3600 μM, and 9000 μM (corresponding to the addition of 10, 20, and 50 μl, respectively, of 5% $HgCl_2$ to 1000 μl blood). Ten sample were evaluated per experiment. The following recalcification times were found:

| Final mercuric chloride concentration | Recalcification time (sec) |
|---|---|
| 0 | 339 ± 134 |
| 1800 μM | 234 ± 110 |
| 3600 μM | 227 ± 93 |
| 9000 μM | 235 ± 148 |

It is apparent from the above data that all three concentrations of mercuric ion produced the equivalent effect; 1800 μM was selected for all further studies unless otherwise noted.

EXPERIMENT IV

EFFECT OF SIMULTANEOUS CALCIUM SALT AND MERCURIC ION ADDITION

To citrated whole blood was added simultaneously mercuric ions (0.9 mM $HgCl_2$) and calcium chloride and the recalcification time determined immediately thereafter. Ten samples were evaluated per experiment. The control sample (calcium salt alone) showed a recalcification time of 9.6±1.8 minutes, versus 7.3±1.9 minutes (p<0.0001) with mercuric ion. Thus, no preincubation of blood with mercuric ion is necessary to demonstrate a significant effect of mercuric ion on recalcification time.

EXPERIMENT V

EFFECT OF MERCURIC ION ON THE RECALCIFICATION TIME WHOLE BLOOD OF PATIENTS UNDERGOING HEPARIN ANTICOAGULANT THERAPY

Recalcification times were determined for patients undergoing anticoagulant therapy with heparin, versus non-anticoagulated patients. In addition, prothrombin times and activated partial thromboplastin times were determined for all patients.

| Measurement (n = 23 for both groups) | Patients not undergoing anti- coagulation therapy | Patients undergoing anticoagulation therapy with heparin |
|---|---|---|
| Prothrombin Time | 10 to 14 seconds (normal range) | 16 ± 5 seconds |
| Activated Partial Thromboplastin Time | 24 to 38 seconds (normal range) | 55 ± 16 seconds |
| Control for below | 291 ± 67 seconds | 475 ± 104 seconds |
| Mercuric ion-activated | 234 ± 57 seconds | 344 ± 109 seconds |

As expected, patients undergoing heparin anticoagulant therapy had longer prothrombin times and activated partial thromboplastin times than non-anticoagulant-treated patients. The value for the control for the mercuric ion-activated recalcification time (no mercuric ion) of the heparin-treated patients was longer than the nontreated patients, also as expected. The mercuric ion-activated recalcification time value with mercuric ion for the treated patients showed a relatively greater reduction (28%) than the nontreated patients (20%). The mercuric ion-activated recalcification time may be a useful marker for more effective heparin anticoagulant therapy monitoring.

In the next experiment, the effect of the level of heparin on recalcification time was determined:

| Sample (n = 8) | Recalcification time in the absence of mercuric ion (seconds) | Recalcification time in the presence of mercuric ion (seconds) |
|---|---|---|
| Control (no heparin) | 266 ± 61 | 164 ± 41 |
| Plus 0.15 U/ml heparin | 364 ± 84 | 249 ± 59 |
| Plus 0.3 U/ml heparin | 517 ± 132 | 314 ± 85 |
| Plus 0.5 U/ml heparin | 918 ± 372 | 566 ± 220 |

Thus, increasing concentrations of heparin prolong the recalcification time of citrated whole blood, both in the absence and in the presence of mercuric ion. The mercuric ion-activated recalcification time may be used to monitor heparin therapy.

EXAMPLE VI

EFFECT OF MERCURIC ION ON WHOLE BLOOD INCUBATED WITH HOMOCYSTEINE

Homocysteine is found in elevated levels in circulation in patients with thrombotic diseases, such as atherosclerosis.

| Sample treatment (n = 12) | Recalcification time (seconds) |
|---|---|
| Control | 247 ± 37 |
| Plus homocysteine (100 μM) | 254 ± 49 |
| Plus mercuric ion (1.8 mM) | 170 ± 42 |
| Homocysteine plus mercuric ion | 145 ± 37 |

Homocysteine alone shows no procoagulant effect when added to citrated whole blood when compared to the control. However, mercuric ion and homocysteine together show a reduced recalcification time when compared to either alone. Therefore, the mercuric ion-activated recalcification time may be used to detect a procoagulant state induced by elevated homocysteine levels.

EXAMPLE VII

EFFECTS OF SILVER ION ON THE RECALCIFICATION TIME OF CITRATED PLASMA

Silver ion was mixed with citrated plasma and the recalcification time determined:

| Sample (n = 7) | Recalcification time (seconds) |
|---|---|
| Control | 584 ± 481 |
| silver nitrate (2.9 mM) | 324 ± 366 |

Silver ion significantly reduced the recalcification time of plasma.

EXPERIMENT VIII

EFFECT OF HEPARIN AND HOMOCYSTEINE ON SILVER ION-ACTIVATED RECALCIFICATION TIME OF WHOLE BLOOD

The effect of heparin and homocysteine on the silver ion-activated recalcification time was assessed as follows:

| Sample (n = 10) | Recalcification time (sec) |
|---|---|
| Control | 311 ± 57 |
| silver nitrate (2.9 mM) | 127 ± 41 |
| heparin (0.25 U/ml) | 524 ± 178 |
| silver nitrate + heparin | 174 ± 90 |
| Control | 305 ± 77 |
| silver nitrate (2.9 mM) | 121 ± 45 |
| homocysteine (100 μM) | 341 ± 86 |
| silver nitrate + homocysteine | 105 ± 46 |

As shown in the above table, silver nitrate reduces the recalcification time of blood. Heparin prolongs the recalcification time as compared to control, as expected, but the combination of heparin and silver nitrate overcomes the majority of the heparin effect.

Furthermore, homocysteine prolongs the recalcification time of blood. Inclusion of silver nitrate potentiates the in-vitro prothrombotic effect of homocysteine.

The effect of silver ion on citrated whole blood containing various concentrations of heparin was studied:

| Sample (n = 8) | Recalcification time in the absence of silver ion (secs) | Recalcification time in the presence of silver ion (secs) |
|---|---|---|
| Control (no heparin) | 277 ± 89 | 72 ± 13 |
| Plus 0.15 U/ml heparin | 355 ± 131 | 96 ± 43 |
| Plus 0.3 U/ml heparin | 484 ± 256 | 122 ± 50 |
| Plus 0.5 U/ml heparin | 748 ± 306 | 198 ± 89 |

Thus, increasing concentrations of heparin prolong the recalcification time in the presence of silver ion. The silver ion-activated recalcification time may be used as an effective monitor of heparin therapy.

EXAMPLE IX

THE EFFECT OF SILVER AND MERCURIC IONS ON TISSUE FACTOR- AND RUSSELLS' VIPER VENOM-ACCELERATED RECALCIFICATION TIME

Tissue factor initiates the extrinsic pathway of blood coagulation. Russells' viper venom accelerates clotting by activating Factors V and X. In the following experiments, tissue factor was used at a final concentration of 0.25% of Prothrombin Time Reagent (tissue factor) and Russells' viper venom at 20 μg/ml. Citrated whole blood was used.

| Sample (n = 8) | Recalcification time (sec) |
|---|---|
| Control | 258 ± 52 |
| Tissue factor (0.25%) | 122 ± 32 |
| silver nitrate (2.9 mM) | 106 ± 25 |
| mercuric chloride (1.8 mM) | 183 ± 63 |
| silver nitrate + tissue factor | 78 ± 20 |
| mercuric chloride + tissue factor | 128 ± 41 |

| Sample (n = 8) | Recalcification time (sec) |
|---|---|
| Control | 259 ± 44 |
| Russells' viper venom (20 μg/ml) | 129 ± 35 |
| silver nitrate (2.9 mM) | 82 ± 43 |
| mercuric chloride (1.8 mM) | 166 ± 35 |
| silver nitrate + venom | 62 ± 24 |
| mercuric chloride + venom | 114 ± 22 |

Tissue factor and Russells' viper venom reduced the clotting time when compared to the controls. The silver and mercuric ion clotting times in the presence of tissue factor or Russells' viper venom are reduced compared to those of the metal ions alone or tissue factor or venom alone. Tissue factor initiates the extrinsic clotting cascade whereas Russells' viper venom activates both Factor V and X of the clotting cascade. Clinical states, including those which are asymptomatic, in which these factors are present in their activated forms are those with increased thrombotic tendencies. These reagents will facilitate a more extensive test of blood samples for coagulopathies.

EXAMPLE X

THE EFFECT OF HIRUDIN ON MERCURIC ION- AND SILVER-ION ACTIVATED RECALCIFICATION TIMES

The antithrombin anticoagulant hirudin was used at a concentration of 0.1 U/ml to evaluate the effect of metal ions on coagulation time.

| Sample (n = 7) | Recalcification time (sec) |
|---|---|
| Control | 281 ± 45 |
| Silver nitrate (2.9 mM) | 114 ± 27 |
| Mercuric chloride (1.8 mM) | 168 ± 18 |
| Hirudin (0.1 U/ml) | 366 ± 49 |
| Hirudin plus silver ion | 103 ± 31 |
| Hirudin plus mercuric ion | 255 ± 75 |

Hirudin in the presence of mercuric ion significantly prolongs clotting time compared to mercuric ion alone. Mercuric ion-activated clotting times may be useful in monitoring patients being treated with hirudin chronically for thrombotic events such as deep vein thrombosis or acutely for various procedures such as angioplasty.

EXAMPLE XI

EFFECT OF HIRUDIN ON ECARIN-, MERCURIC ION-, AND SILVER ION- ACTIVATED RECALCIFICATION TIMES

Ecarin is the venom of the snake *Echis carinatus*. It activates prothrombin, even in anticoagulated blood, to more rapidly generate thrombin. Ecarin (5 μl of a 0.01 mg/ml solution per 340 μl of blood) was placed directly into a cuvette into which the blood sample was added.

| Sample (n = 4) | Recalcification time (sec) |
|---|---|
| Control | 276 ± 72 |
| silver nitrate (2.9 mM) | 75 ± 24 |
| mercuric chloride (1.8 mM) | 151 ± 35 |
| Ecarin (150 ng/ml) | 131 ± 27 |
| Hirudin (0.1 U/ml) | 239 ± 103 |
| Ecarin plus silver nitrate | 68 ± 10 |
| Ecarin plus mercuric chloride | 113 ± 14 |
| Hirudin plus ecarin | 169 ± 55 |
| Hirudin plus silver nitrate | 95 ± 20 |
| Hirudin plus mercuric chloride | 249 ± 65 |

These data show that in the absence of hirudin, silver ion, mercuric ion, and ecarin all shorten clotting time compared to the control. In the presence of hirudin all of the clotting times were elevated. Therefore, these reagents alone or in combination may be useful for monitoring hirudin and heparin anticoagulant therapy.

EXAMPLE XII

EFFECT OF LEAD AND CADMIUM ION ON RECALCIFICATION TIME

In this experiment the effects of lead nitrate and cadmium sulfate on clotting time were evaluated. A 5% aqueous solution of these compounds was used.

| Sample (n = 8) | Recalcification time (sec) |
|---|---|
| Control | 315 ± 78 |
| silver nitrate | 97 ± 35 |
| mercuric chloride | 196 ± 47 |
| lead nitrate | 866 ± 63 |
| cadmium sulfate | 902 ± 3 |

As opposed to the shortening of recalcification time caused by mercuric and silver ion, lead and cadmium ion significantly prolong recalcification. This effect may be used to monitor various coagulopathies.

EXPERIMENT XIII

EFFECT OF SILVER ION AND MERCURIC ION ON THROMBIN-ACCELERATED RECALCIFICATION TIME

Thrombin, a potent procoagulant, reacts with fibrinogen to produce fibrin, the clot. Thrombin is used in fibrin glues (comprising thrombin, fibrinogen and other reagents) to seal wounds and to stop bleeding, and as a hemostatic agent in spray form, i.e., topical thrombin.

Thrombin was used at a concentration (0.017 U/ml) that was not sufficient to clot anticoagulated blood without the addition of calcium.

| Sample (n = 8) | Recalcification time (sec) |
|---|---|
| Control | 262 ± 37 |
| thrombin (0.017 U/ml) | 143 ± 24 |

-continued

| Sample (n = 8) | Recalcification time (sec) |
| --- | --- |
| silver nitrate (2.9 mM) | 104 ± 18 |
| mercuric chloride (1.8 mM) | 167 ± 35 |
| thrombin plus silver nitrate | 79 ± 17 |
| thrombin plus mercuric chloride | 116 ± 37 |

Both mercuric ion and silver ion potentiate the thrombotic effects of thrombin.

EXPERIMENT XIV

EFFECT OF MERCURIC ION AND SILVER ION ON BLOOD VISCOSITY

A SONOCLOT(R) viscosity analyzer was used to evaluate the effects of mercuric ion and silver ion on the viscosity of anticoagulated whole blood.

| Sample (n = 8) | Viscosity units |
| --- | --- |
| Control | 25 ± 2.9 |
| mercuric chloride (2.9 mM) | 27 ± 4.8 |
| silver nitrate (1.8 mM) | 29 ± 3.6 |

Both silver ion and mercuric ion significantly increase the viscosity of blood.

EXAMPLE XIV

EFFECT ON RECALCIFICATION TIME OF THE COMBINATION OF SILVER ION AND MERCURIC ION

The effect of the combination of mercuric ion and silver ion was evaluated. Mercuric nitrate was used as the source of mercuric ion instead of the chloride salt in these experiments, because the latter in combination with silver ion would result in the precipitation of silver chloride.

| Sample (n = 6) | Recalcification time (sec) |
| --- | --- |
| Control | 354 ± 91 |
| silver nitrate (2.9 mM) | 116 ± 54 |
| mercuric nitrate (1.8 mM) | 245 ± 99 |
| silver nitrate plus mercuric nitrate | 117 ± 61 |

Although on average there were no significant changes between silver ion alone and silver plus mercuric ion, in one of the six samples, a 27% reduction in recalcification time by the two metal ions alone compared to silver ion alone was observed.

EXAMPLE XV

EFFECT OF SILVER ION ON RECALCIFICATION TIME OF PLATELET-DEPLETED AND PLATELET-RICH PLASMA

Platelets, which contain factors which initiate the blood clotting process, are often provided to patients who are platelet-deficient and have as a result a reduced coagulability of the blood. Platelets are provided to such patients in the form of a transfusion of platelet-rich plasma, which is prepared from whole blood by a slow-speed centrifugation process whereby the red blood cells and white blood cells are separated but the lighter platelets are left with the plasma. In contrast, a high-speed centrifugation and removal of all solid components of blood provides platelet-depleted plasma. The latter contains blood coagulation factors, but no platelets.

The effect of silver ion on the recalcification time of these plasma preparations was evaluated.

| Sample (n = 8) | Recalcification time (seconds) |
| --- | --- |
| Control, citrated whole blood | 262 ± 26 |
| citrated whole blood plus silver nitrate (2.9 mM) | 109 ± 20 |
| Control, platelet-rich plasma | 314 ± 70 |
| platelet-rich plasma plus silver nitrate | 83 ± 30 |
| Control, platelet-depleted plasma | 353 ± 62 |
| platelet-depleted plasma plus silver nitrate | 128 ± 32 |

The addition of silver ion to citrated whole blood and to both of the plasma preparations significantly reduces the clotting time as compared to control values. Thus, silver ion-activated recalcification time may be used to assess the coagulability of citrated whole blood, platelet-rich plasma and plasma, and provide an assessment of platelet function.

EXAMPLE XVI

EFFECT OF METAL IONS AND ANIONS ON RECALCIFICATION TIME OF WHOLE BLOOD AND PLASMA

In this experiment the effects of single and combination metal ions or anions on the clotting time of citrated whole blood were evaluated. 5% aqueous solutions of these compounds were used, with an incubation time of 10 minutes, following the general methodology above.

| Sample (n = 4) | Recalcification time (sec) |
| --- | --- |
| Control | 245 ± 27 |
| silver nitrate | 110 ± 28 |
| sodium tungstate | 331 ± 23 |
| stannous chloride | 217 ± 13 |

| Sample (n = 8) | Recalcification time (sec) |
| --- | --- |
| Control | 267 ± 81 |
| silver nitrate | 109 ± 26 |
| copper sulfate | 555 ± 125 |

The following experiments were performed with citrated plasma.

| Sample (n = 3) | Recalcification time (sec) |
| --- | --- |
| Control | 501 ± 241 |
| silver nitrate | 159 ± 35 |
| stannous chloride | 307 ± 75 |
| copper sulfate | 1761 ± 934 |
| barium chloride | 636 ± 222 |

Based on the above experiments, copper (II) prolongs the recalcification time of whole blood and plasma, as does barium; tin (II) reduces the recalcification of plasma but has no effect on that of whole blood. The recalcification times in the presence of redox active metal salts such as tin (II) and copper (II) are useful clinical markers of the effects of therapeutics, and on the treatment and progression of disease.

EXAMPLE XVII

THE EFFECT OF COMBINATIONS OF METAL IONS AND ANIONS ON RECALCIFICATION TIME OF WHOLE BLOOD

The effect of combinations of copper (II) with tin (II) or selenous acid were evaluated on whole blood. Selenous acid was used at a stock concentration of 2.5%.

| Sample (n = 4) | Recalcification time (sec) |
| --- | --- |
| Control | 278 ± 43 |
| copper sulfate | 951 ± 240 |
| stannous chloride | 252 ± 18 |
| selenous acid | 276 ± 7 |
| copper sulfate plus stannous chloride | 429 ± 92 |
| copper sulfate plus selenous acid | 585 ± 83 |

Tin (II) had no effect on whole blood recalcification time, but markedly attenuated the prolonged recalcification time induced by copper (II). Selenous acid had a similar effect in that it had no effect alone but reduced the prolonged recalcification time in the presence of copper (II). Thus, coagulation tests employing different redox active metal cations or anions and their combinations may be used to monitor oxidative stress in blood and plasma, and direct appropriate treatments thereto.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

Various publications in addition to the immediately foregoing are cited herein, the disclosures of which are incorporated by reference in their entireties.

What is claimed is:

1. A method for analyzing the blood of a mammal to determine the presence or development of pathology related to abnormalities in the coagulation state of the blood of said mammal sequentially comprising:

(1) collecting a sample of whole blood from said mammal;

(2) preparing at least two aliquots of whole blood from said sample;

(3) adding an amount of at least one metal ion reagent to one of said aliquots, said at least one metal ion reagent being a solution comprising a salt of a metal selected from the group consisting of lead, cadmium, tungstate, copper, and any combination thereof;

(4) measuring a clotting time of the aliquots; and (5) correlating a prolongation in clotting time by said at least one metal ion reagent to the presence or development of abnormalities in the coagulation state of the blood of said mammal.

2. The method of claim 1 wherein the sample of blood of step (1) is collected in the presence of a calcium-binding anticoagulant, and the measurement of clotting time of step (4) is initiated by the addition of a calcium salt to said aliquots.

3. The method of claim 1 wherein a modulator of blood coagulation is added to at least one of said aliquots at or prior to step (4).

4. The method of claim 3 wherein the modulator is selected from the group consisting of tissue factor, prothrombotic venoms, thrombin, ecarin, homocysteine, platelet activating factor, fibrinogen, kaolin, celite, adenosine diphosphate, arachidonic acid, collagen, ristocetin, Protein C, protein S, antithrombin III, thrombomodulin, tissue plasminogen activator, urokinase, streptokinase, Von Willebrand Factor, cancer cell extracts, amniotic fluid, therapeutic drugs, and combinations thereof.

5. The method of claim 4 wherein the prothrombotic venom is Russells' viper venom.

6. A diagnostic kit for analyzing the blood of a mammal to determine the presence or development of pathology suspected of causing abnormalities in the coagulation state of the blood of said mammal, said kit comprising a container containing an anticoagulant, and at least one container containing a metal ion reagent, said metal ion reagent being a solution comprising a salt of a metal selected from the group consisting of lead, cadmium, barium, copper, tin, tungstate, and any combination thereof.

7. The kit of claim 6 further comprising a container containing a modulator of blood coagulation.

8. The kit of claim 7 wherein the modulator is selected from the group consisting of tissue factor, prothrombotic venoms, thrombin, ecarin, homocysteine, platelet activating factor, fibrinogen, kaolin, celite, adenosine diphosphate, arachidonic acid, collagen, ristocetin, Protein C, protein S, antithrombin III, thrombomodulin, tissue plasminogen activator, urokinase, streptokinase, Von Willebrand Factor, cancer cell extracts, amniotic fluid, therapeutic drugs, and combinations thereof.

9. The kit of claim 8 wherein the prothrombotic venom is Russells' viper venom.

10. A method for analyzing the blood of a mammal to determine the presence or development of pathology related to abnormalities in the coagulation state of the blood of said mammal sequentially comprising:

(1) collecting a sample of whole blood from said mammal in the presence of an anticoagulant;

(2) preparing at least two aliquots of plasma from said sample;

(3) adding an amount of at least one metal ion reagent to one of said aliquots, said at least one metal ion reagent being a solution comprising a salt of a metal selected from the group consisting of silver, mercury, barium, copper, tin, and any combination thereof;

(4) measuring a clotting time of the aliquots; and (5) correlating a difference in clotting time between said aliquots to the presence or development of abnormalities in the coagulation state of the blood of said mammal.

11. The method of claim 10 wherein said silver salt is silver nitrate.

12. The method of claim 10 wherein said mercuric salt is mercuric chloride.

13. The method of claim 10 wherein a modulator of blood coagulation is added to at least one of said aliquots at or prior to step (4).

14. The method of claim 13 wherein the modulator is selected from the group consisting of tissue factor, pro-thrombotic venoms, thrombin, ecarin, homocysteine, platelet activating factor, fibrinogen, kaolin, celite, adenosine diphosphate, arachidonic acid, collagen, ristocetin, Protein C, protein S, antithrombin III, thrombomodulin, tissue plasminogen activator, urokinase, streptokinase, Von Willebrand Factor, cancer cell extracts, amniotic fluid, therapeutic drugs, and combinations thereof.

* * * * *